United States Patent [19]

Buffet

[11] Patent Number: 4,574,814

[45] Date of Patent: Mar. 11, 1986

[54] SLIDING COAXIAL PROBE FOR A PACEMAKER

[75] Inventor: Jacques Buffet, Le Raincy, France

[73] Assignee: Cardiofrance-Compagnie Francaise d'Electrocardiologie, France

[21] Appl. No.: 396,397

[22] Filed: Jul. 8, 1982

[30] Foreign Application Priority Data

Jul. 31, 1981 [FR] France .................................. 81 14944

[51] Int. Cl.[4] .............................................. A61N 1/05
[52] U.S. Cl. .................................. 128/786; 128/419 P
[58] Field of Search .............................. 128/784–786, 128/419 P

[56] References Cited

U.S. PATENT DOCUMENTS

| | | | |
|---|---|---|---|
| 3,769,984 | 11/1973 | Muench | 128/786 |
| 3,865,118 | 2/1975 | Bures | 128/786 |
| 4,271,847 | 6/1981 | Stokes | 128/786 |
| 4,289,144 | 9/1981 | Gilman | 128/785 |
| 4,327,747 | 5/1982 | Gold | 128/784 |
| 4,332,259 | 6/1982 | McCorkle, Jr. | 128/786 |

FOREIGN PATENT DOCUMENTS

| | | | |
|---|---|---|---|
| 2605590 | 8/1977 | Fed. Rep. of Germany | 128/419 P |
| 2446001 | 8/1980 | France | 128/786 |

*Primary Examiner*—Lee S. Cohen
*Attorney, Agent, or Firm*—Darby & Darby

[57] ABSTRACT

A probe is provided for a pacemaker which is associated by one of its end portions with the pacemaker and by its opposite end portion with the auricle and the ventricle of the heart. It comprises two conductors which form a one-piece assembly and which are associated with each other by means allowing them to slide axially with respect to each other, namely two tubes or sleeves fitting one into the other and movable with respect to each other. An annular space is provided between said tubes.

7 Claims, 7 Drawing Figures

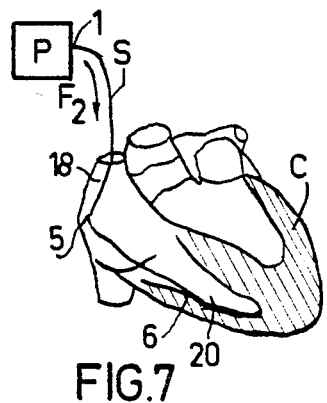
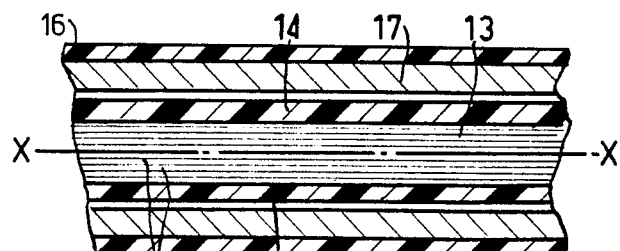
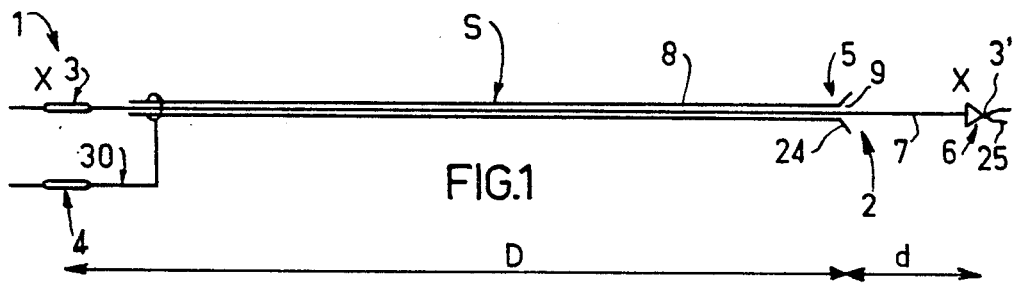
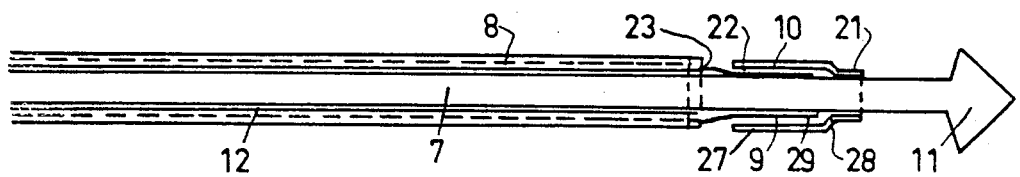
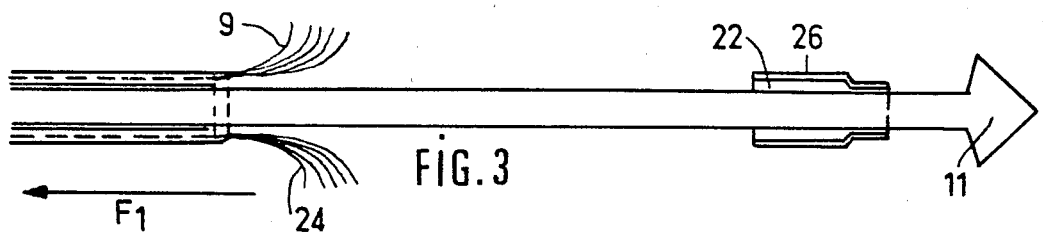
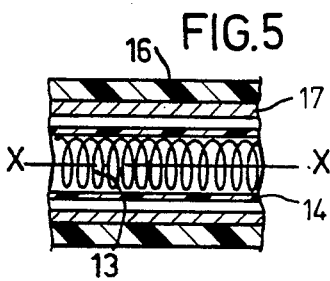
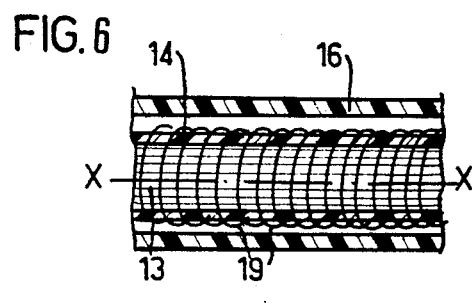

SLIDING COAXIAL PROBE FOR A PACEMAKER

BACKGROUND OF THE INVENTION

The invention relates to a probe intended to be associated more especially with an implanted pacemaker and the cardiac muscle.

A system is already known having two separate probes associated, at a first end, with a pacemaker and, at the other end, respectively with the auricle and with the ventricle. Such devices are more especially, but not exclusively used for a pacemaker synchronous with the auricle. The activity of the auricle is sensed by a first probe and stimulation of the ventricle is achieved by means of the second probe.

Pacemakers are also known of the bicavitary type, with which two probes are associated, one being fixed by its end to the auricle and the other being fixed by its end to the ventricle.

In general, fixing of the probe to the ventricle is no major problem. On the other hand, fixing to the auricle is difficult and implantation thereof is not easy. Thus, pacemakers synchronous with the auricle are very rarely used at the present time, although they provide pacemaking of the ventricle of a patient adapted to the rhythm of the auricle and although they are well adapted for young subjects.

A single coaxial non sliding probe is also known, comprising two end connections, fixed with respect to each other, intended to be associated respectively with the auricle and with the ventricle. Thus, with a standard probe of known type it is very difficult to adapt it to different patients.

The aims of the invention are then to palliate these drawbacks.

A first aim is to provide a probe, more especially for a heart pacemaker, whose ends can be correctly coupled respectively to the auricle and to the ventricle.

A second aim is to provide a single probe comprising a connection with the auricle and a connection with the ventricle, situated at an end portion, adaptable whatever the distance between the auricle and the ventricle.

SUMMARY OF THE INVENTION

To attain these aims, the invention proposes a probe intended to be associated more especially with a pacemaker by one of its ends and by two connections situated at its opposite end portion, respectively with the auricle and ventricle of the heart, said probe further comprising two conductors forming a one-piece assembly and associated with one another by means allowing them to slide axially with respect to each other.

According to another feature of the invention, the heart connections are spaced apart along the axis of the probe, by a distance which is therefore variable.

Such a probe presents then the advantage of having two heart connections, which, because of the mobility of the two conductors with respect to each other, are disposed at a variable, i.e. adjustable, distance which may be adapted according to requirements. By sliding one conductor relative to the other, the distance between the two connections is varied and the probe may be adapted to the heart of any patient.

According to another feature of the invention, the axial sliding means for the two conductors are two tubes, or sleeves, fitting one in the other and movable with respect to each other through a radial space provided therebetween, or opposing free motion.

BRIEF DESCRIPTION OF THE DRAWINGS

The other features of the invention will be well understood from the following description, with reference to the accompanying drawings in which:

FIG. 1 is a schematical view of the probe of the invention;

FIG. 2 is an enlarged view of the end portion of the probe intended to be associated with the heart, before it is placed in position;

FIG. 3 is a view of the end portion of the probe after being placed in position;

FIG. 4 is a schematical section of a first embodiment of the conductors of the probe of the invention;

FIG. 5 is a section of a second embodiment of the conductors;

FIG. 6 is a section of a third embodiment of the conductors; and

FIG. 7 is a schematical view of a probe in accordance with the invention into the heart.

DESCRIPTION OF THE PREFERRED EMBODIMENTS

According to the invention, there is provided a probe S whose end portion 1 is intended to be associated mechanically and electrically, in a way known per se, by means of two connections 3,4 with a pacemaker P, and respectively with the ventricle and auricle of the heart by means of two electrical and mechanical connections 5,6, one connection 5 being set back from the other terminal 6, and both being situated at its other end portion 2.

The extended probe S is rectilinear, has an axis XX and a form substantially at least pseudo cylindrical about axis XX. Probe S is flexible so as to be able to be adapted to the specific path between the pacemaker P and the heart C. On the whole, and subject to what is explained in detail hereafter, it is substantially inextensible.

According to one feature of the invention, probe S comprises two electric conductors 7,8 forming a one-piece assembly, i.e. inseparable, but associated with each other by means allowing them to slide axially with respect to one another along axis XX. The two conductors 7,8 correspond, respectively, to the terminal heart connection 6 and the set-back heart connection 5.

The heart connections 5,6 are spaced apart from each other along axis XX of probe S by a distance d, which distance is variable when the conductors 7,8 are moved with respect to each other. The connection 6 forms, strictly speaking, the corresponding free end of probe S when the connection 5 is set back to the rear of connection 6.

The heat connections 5,6 are situated, respectively, at the free ends of conductors 7,8, on the same side as end portion 2. By sliding, for example, conductor 8 with respect to conductor 7 in the direction of arrow $F_1$, i.e. in the direction from the end 2 of the probe towards the end 1 thereof, the distance d may be varied, in this case increased, between the heart connections 5,6. One of the conductors, preferably conductor 8, comprises slack at its end portion 30, which portion is intended to be associated with the pacemaker P, so as to allow relative sliding.

According to another feature of the invention, probe S comprises unidirectional means 10 for locking conductor 8 with respect to conductor 7. The locking means 10 prevent conductor 8 from sliding with respect to conductor 7 in the direction opposite arrow $F_1$, beyond a limit position, corresponding to the minimum value of d.

The unidirectional locking means 10 are situated, preferably, at the level of the set-back connection 5. Preferably, the unidirectional locking means 10 are formed by a ring 10 coaxial with the conductors 7,8, one end 21 of which is fixed rigidly to conductor 7 and the opposite end 22 of which, directed towards connection 5, abuts against an annular shoulder 23 on conductor 8 in the immediate vicinity of its free end.

The heart connections 5,6 are preferably formed by a plurality of electricity conducting fibers 9,3', constituting the endmost parts of fibers forming the respective conductors, capable of being anchored in the heart muscle and diverging from axis XX of probe S form sort of resiliently deformable "feather dusters" 24,25. The fibers assume this shape of a feather duster in the absence of any external action. Thus, when the fibers are inserted into the heart, the cardiac zone which is in contact with the end of the fibers is determined by the intersection of this cardiac surface with the envelope of the fibers. Preferably, the fibers are situated in a cone with axis XX whose larger base is directed towards the free end of the fibers.

The intersection surface between the cardiac surface and the envelope of the fibers is then greater than that which would be obtained if the fibers were parallel to axis XX inside a cylinder, so anchoring the fibers in the heart muscle is improved. Fibers 9,3' may for example be carbon fibers.

According to another feature of the invention, probe S comprises means 26 for the temporary effacement of the feather dusters 24,25 formed from fibers of at least one heart connection 5,6 during positioning thereof, preferably the set-back connection 5. More particularly, means 26 for effacing fibers 9 are formed by the unidirectional means 10 for locking conductor 8 with respect to conductor 7. The effacement means are thus formed by ring 10 gripping round the feature duster of fibers 24. Ring 10, besides its end part 21 which is attached to conductor 7 and directed towards connection 6, and its end portion 22 abutting against the shoulder 23 of conductor 8, has a lateral part 27 for holding the feather duster 24 and a middle part 28 for frontal locking of the feather duster 24. The lateral part 27 and conductor 7 are coaxial, pseudo cylindrical and define an annular space 29 for effacement of the feather duster 24. The effacement means 26 are then permanently integrated with the probe and form an integral part thereof. They are then not external means. The effacement means 26 are only active during positioning of the probe. At this time the two conductors 7,8 have a particular relative position in which the set-back heart connection 5 is the closest to the heart connection 6 and is adjacent the free end 11 of probe S. Thus the distance d is minimum. When the two conductors 7,8 are caused to slide with respect to one another in the direction of arrow $F_1$, i.e. away from the position for placing the probe, the set-back connection 5 and connection 6 are spaced apart from one another and the distance d increases. Then the effacement means become ineffective and fibers 9 are freed from ring 10 to form the feather duster 24.

According to another feature of the invention, the means for axial sliding of the two conductors 7,8 include two tubes or sleeves fitting one in the other and movable with respect to one another. A radial space or clearance 12 is provided between the tubes. This space allows axial sliding of conductors 7,8.

According to a first variation of the invention, the internal conductor 7 is substantially cylindrical in shape about axis XX and is formed from an electricity conducting wire 13 embedded in an insulating sleeve 14. The conducting wire 13 is formed from a plurality of fibers 15 of an electricity conducting material, preferably carbon fibers. The insulating sleeve 14 is for example formed from polyethylene. The electrically conducting wire 13 may be disposed in an external insulating sleeve 14, it being also, for example, made from polyethylene. Furthermore, a spiral shaped conducting wire 13 (FIG. 5) may be provided, winding helically about axis XX.

According to this first variation, the external conductor 8 is formed by an external conducting wire 17 embedded in an external insulating sleeve 16 which is coaxial with sleeve 14 of the internal conductor 7. This external electrically conducting wire 17 may be formed, for example, from a plurality of electrically conducting fibers, namely carbon fibers. Between the internal sleeve 14 and the external sleeve 16, a space or clearance 12 is provided, as was mentioned above, for allowing the two conductors 7,8 to slide.

In a second variation, the external conductor 8 is formed by a spiralled conducting wire 19 winding helically about the insulating sleeve 14 between this latter and a coaxial external sleeve 16. Between the turns of the spiral wire 19 and the insulating sleeve 14 there exists an annular space or clearance 12 which allows conductor 8 to slide with respect to conductor 7. Thus, the turns of wire 19 do not grip sleeve 14. The internal and external sleeves are mobile with respect to each other, freely or with an easy fit, because of the clearance 12 which is provided therebetween.

Probe S of the invention is placed in position in the following way: the free end 11 of probe S is inserted in the direction of arrow $F_2$, which is directed in the opposite direction to arrow $F_1$, into a vein, preferably situated at the base of the neck. The means for effacing feather duster 24 are then preferably active and fibers 9 are effaced. The two conductors 7,8 are then not movable with respect to one another, the unidirectional means 26 for locking conductor 8 with respect to conductor 7 being active so that the end portion 22 of these means abut against the shoulder 23 of conductor 8, as was explained above. The free end 11 of probe S is inserted as far as the ventricle 20, by passing through the auricle 18. Then the heart connection 6 is released and fixed in ventricle 20. Thus, during insertion of probe S into the vein and until the heart connection 6 is fixed in the ventricle 2, the two conductors respectively internal and external 7,8 have moved simultaneously and there has been no relative sliding with respect to each other. After the heart connection 6 is fixed, external conductor 8 is moved axially in the direction of arrow $F_1$. The means 26 for effacing fibers 9 are then inactive and these latter are released. Since they are resiliently deformable, they move naturally away from axis XX to assume the shape of a feather duster 24. Finally, at the time when the fibers are at the level of the optimum point for auricular pick-up, they will be fixed in auricle 18.

Thus, with the distance d between the auricular pick-up point and the ventricular pick-up point varying depending on the patients, the probe may be adapted by simply sliding external conductor 8 to a greater or lesser extent with respect to internal conductor 7 in the direction of arrow $F_1$ directed from the end portion 2 of the probe associated with the heart muscle to the end portion 1.

What is claimed is:

1. A cardiac probe having a longitudinal axis comprising:

internal and external conductors arranged coaxially and being separated from each other by an annular space so as to permit the longitudinal sliding of one with respect to the other, at least one of said conductors being in the form of a plurality of electrically conducting fibers;

a first electrical and mechanical connection located at one end of the two conductors and being adapted to be connected to a cardiac stimulator;

second and third electrical and mechanical connections at the other end of said internal and external conductors, respectively, said second and third connections being longitudinally spaced from each other such that the internal conductor extends beyond the external conductor, said internal and external conductors also being adapted to be connected to the auricle and the ventricle of a heart, respectively, via said second and third connections; and unidirectional means for locking the internal and external conductors with respect to each other to prevent the sliding thereof beyond a certain distance, said unidirectional means including a ring rigidly fixed to one of the conductors and engaging the other at a certain sliding distance, such engagement further preventing the fibers from diverging from the axis of the probe and the absence of such engagement allowing the fibers to diverge and form a resiliently deformable feather-duster array adapted for contacting the heart as one of said second and third connections.

2. The probe as claimed in claim 1, wherein said conductors are substantially cylindrical in shape, and coaxial with each other and the axis of the probe.

3. The probe as claimed in claim 1 wherein the plurality of electricity conducting fibers, are carbon fibers.

4. The probe as claimed in claim 3, wherein at least one conductor of said two conductors is formed by a conducting wire substantially helical in shape, winding about the axis of the probe.

5. The probe as claimed in any one of claims 1, 2, 3 or 4, wherein at least one conductor of said two conductors is embedded in an insulating sleeve.

6. The probe as claimed in claim 1, wherein said ring forms an integral part of the probe, said ring including a first end portion fixed to said internal conductor, a lateral part for holding said fibers in place and a median part for frontal locking of said fibers, said lateral part and said internal conductor defining an annular effacing space.

7. The probe as claimed in claim 6, wherein said unidirectional means for locking said external conductor with respect to said internal conductor are formed by the end portion of said ring abutting against an annular shoulder on said external conductor.

* * * * *